June 12, 1962 G. MERRILL Plant Pat. 2,153

PEACH TREE

Filed April 27, 1961

WITNESS

Addison E. Avery

INVENTOR

GRANT MERRILL

HUEBNER & WORREL

ATTORNEYS

BY Richard M. Worrel

United States Patent Office

Plant Pat. 2,153
Patented June 12, 1962

2,153
PEACH TREE

Grant Merrill, P.O. Box 392, Red Bluff, Calif.

Filed Apr. 27, 1961, Ser. No. 106,137
1 Claim. (Cl. 47—62)

The present invention relates to a peach tree and more particularly to a new and distinct variety thereof broadly characterized by being a medium sized tree with distinctly wavy and crinkled leaves and having fruit which is highly colored, large, firm, generally round, freestone, of excellent shipping quality, good flavor and texture, which ripens late in the season with Merrill Fiesta (Plant Patent No. 1,099), and which has yellow flesh which is firm but not tough.

Because of the rich soil and favorable climatic environment prevailing in most of the commercial peach farming areas of California, peach trees tend to produce rank growth and dense shade resulting in serious impairment of the coloring of the fruit. Inasmuch as most fruits rely on eye appeal for their sales, color impairment is highly undesirable. A primary object to the plant breeding procedures which have resulted in the development of this new peach variety has been to achieve a highly colored, red peach which achieves intense color even under conditions of rank growth and dense shade.

Another object has been to produce a peach that is firm when fully ripe, so that it may be more cheaply harvested and packed, but which will soften after harvest, as in retail stands, to a fine textured, melting fleshed freestone.

Another object has been to provide an improved late bearing peach tree.

Another object has been to achieve a peach tree somewhat similar to the Merrill Fiesta but producing fruit of markedly higher color.

Another object has been to provide a peach tree somewhat similar to the Merrill Splendor (Plant Patent No. 1,257) but which produces fruit which ripen appreciably later.

Further objects and advantages will become apparent in the subsequent description in the specification.

In the drawing which is a water color painting:

Figure 1:
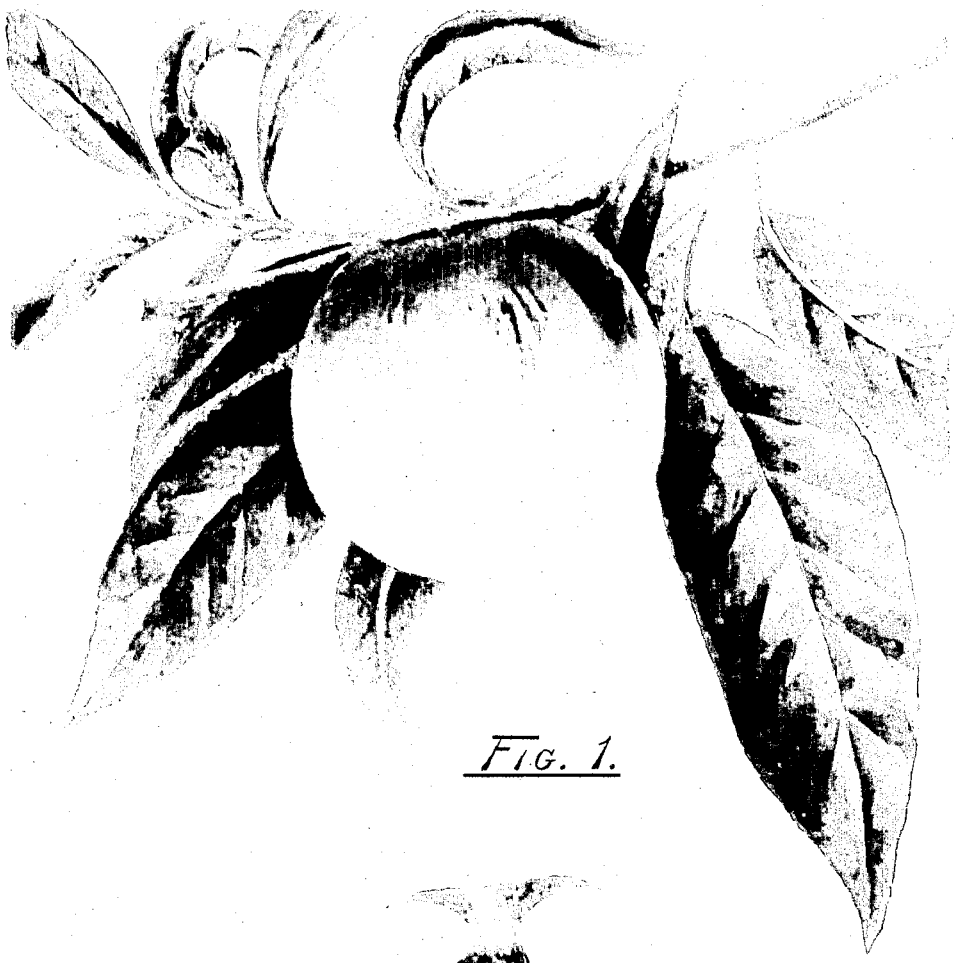
FIG. 1 illustrates characteristic leaves and a mature peach borne by a twig of the subject variety.
Figure 2:
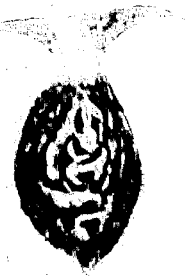
FIG. 2 is a section on the suture plane of a peach of the subject variety showing characteristic flesh and stone coloration.

The most distinctive characteristics of the instant variety of peach tree are its medium size, late ripening, its production of large, firm, yellow-fleshed, highly colored freestone peaches, and its distinctly wavy and crinkled leaves.

The instant variety most nearly resembles the Merrill Splendor (Plant Patent No. 1,099) but is an improvement thereof in that the tree is smaller, the blossoms are self fertile, the leaves are more crinkly and wavy, and the fruit ripens about two weeks later.

This new variety of peach tree was produced by me on my farm near Red Bluff, Tehama County, California from a seedling of unknown parentage. For many years, I have hybridized plants, particularly peach trees, in the development of new varieties. The parentage is carefully selected, the hybridizing carefully performed, and exacting records maintained. However, in this instance, the new variety resulted from a seed of a group which were obtained from the hybridizing work but which had become mixed and their specific parentage unidentifiable.

The present variety was asexually propagated by budding onto nearly seedlings growing on my farm at Red Bluff, Tehama County, California. When these buds came into bearing in September, 1960, the fruit and other characteristics of this peach tree proved to be identical with the original peach tree.

Referring more specifically to the pomological characteristics of this new and distinct variety of peach tree, the following have been observed under the ecological conditions prevailing at my farm near Red Bluff, Tehama, County, California, and is an outline description thereof. All major color plate identifications are by reference to Maerz and Paul Dictionary of Color.

*Tree*

Shape: Medium size, with medium spread, productive and regular bearer.

Trunk: Medium stocky, medium shaggy, brownish grey.

Branches: Older branches, greyish and shaggy; younger branches brown to medium brown and smoother, with numerous medium size lenticels.

Leaves (selected from midportion of vigorous unbranched terminal shoots 12" to 18" long):

*Length.*—5" to 7".

*Width.*—1¼" to 1½".

*Form.*—Medium sized, lanceolate, tip acuminate, medium thick.

*Color.*—Upper surface medium green (22–L–9). Lower surface, light green (22–K–4). Midrib on lower surface, greenish yellow (17–J–1).

*Class* (Meader and Blake: Proceedings Am. Soc. Hor. Sc., vol. 37, page 206).—Class 3 to 4.

*Margin.*—Crenate.

*Petiole.*—Medium length, medium slender.

*Stipules.*—At base of leaf, falling off early.

*Glands.*—1 to 7, average 3 to 4, mostly alternate, medium to small in size, reniform, light green, position mostly on petiole but a few on base of leaf.

Flower buds: Medium size, medium length, plump, free, pubescent.

Flowers: Bloom approximately midseason with Fay Elberta (unpatented).

*Color.*—Salmon pink.

*Size.*—Small.

*Anthers.*—Orange.

*Pollen.*—Moderately abundant.

*Fruit*

Maturity when described, eating ripe, about September 15 to September 30.

Size: Large.

*Axial diameter.*—2½" to 2¾".

*Transverse in suture plane.*—2⅝" to 2⅞".

*Right angles to suture plane (cheek to cheek).*—2⅝" to 2⅞".

Form: Fairly uniform, globose to slightly compressed axially.

*Suture.*—Distinct, shallow, extends from base to apex, has slight depression beyond pistil point.

*Ventral surface.*—Rounded, slightly lipped throughout on most. Lips usually unequal.

*Cavity.*—Round to somewhat elongated in suture plane, with suture usually showing on both sides.

*Depth.*—¼" to ½"; breadth, ¾" to 1¼".

*Markings.*—Red on most with yellow where twig or leaf shades the fruit.

*Base.*—Mostly retuse.

*Apex.*—Mammiform to cuspidate.

*Pistil point.*—Apical, often sharply pointed.

*Stem.*—¼" to ⅜"; diameter, ⅛" to 3/16"; adheres to the stone in a few cases.

*Skin.*—Medium thick, medium tender, not astringent or bitter, tenacious to flesh.

*Tendency to crack.*—None.

*Color.*—Under color bright golden yellow (10–L–5) to orange yellow (10–K–7) to red orange (4–L–11) over one half of the surface, with red-brown (7–L–6) streaks.

Flesh:

*Color.*—Mostly golden yellow (9–L–4), with orange color near the skin (9–K–6), and with light red near the stone (4–K–3).

*Amygdalin.*—Moderate.

*Juice.*—Moderate.

*Texture.*—Firm, meaty to melting.

*Fibers.*—Few, fine.

*Ripens.*—Evenly to slightly earlier toward base.

*Flavor.*—Mild, subacid, delicate, vinous.

*Aroma.*—Moderate.

*Eating quality.*—Good.

*Darkening.*—Does not darken when exposed to air.

Stone: Free, but adheres some to the flesh on the ventral edge near the base.

*Fibers.*—Short.

*Size.*—Length, 1 7/16" to 1 11/16"; breadth, 15/16" to 1 1/4"; thickness, 3/8" to 5/8".

*Form.*—Lanceolate, tip acuminate.

*Base.*—Usually slightly oblique.

*Hilum.*—Oval.

*Apex.*—Acuminate.

*Sides.*—Mostly slightly unequal.

*Surface.*—Irregularly furrowed near the base, pitted toward center.

*Pits.*—Circular to elongated. Ventral edge—thick without wing. Dorsal edge—usually two ridges toward base and center and usually discontinuous toward apex.

*Color of stone.*—Light brown (14–L–12) to dark brown (8–L–6) when first open. The pit dries to a light tan (12–L–9).

*Tendency to split.*—Little.

Use: Market, local, dessert.

Eating quality: Good.

Shipping quality: Good.

It is to be understood that normal variations in the described characteristics of the new variety peach tree result from environmental changes, such as in climate and soil conditions, and from changes in cultural practices, such as in pruning, thinning, fertilizing, spraying, irrigating and the like. The description is that of the variety produced under the ecological conditions prevailing at my farm at Red Bluff, Tehama County, California, and the characteristics are found to hold true in asexual reproduction of the variety.

Having described and illustrated my new variety of peach tree, what I claim as new and desire to secure by Letters Patent is:

A new and distinct variety of peach tree, substantially as illustrated and described, characterized by being a medium sized tree with distinctly wavy and crinkled leaves and having fruit which is highly colored, large, firm, with excellent shipping qualities, generally round with yellow flesh, which is almost completely free from the pit, firm but not tough, good flavor, which ripens very late in the season with Merrill Fiesta (Plant Patent No. 1,099) and which most nearly resembles Merrill Splendor (Plant Patent No. 1,257) but ripens about two weeks later, has self fertile blossoms, is a smaller tree, and has said distinctive crinkled and wavy leaves.

No references cited.